United States Patent
Fu et al.

(10) Patent No.: US 12,378,569 B2
(45) Date of Patent: Aug. 5, 2025

(54) GBWOX3A GENE AND APPLICATION THEREOF IN PLANT TISSUE CULTURE

(71) Applicant: Nanjing Forestry University, Nanjing (CN)

(72) Inventors: Fangfang Fu, Nanjing (CN); Liangjiao Xue, Nanjing (CN); Fuliang Cao, Nanjing (CN); Anqi Zhao, Nanjing (CN); Wei Xu, Taizhou (CN); Pingjun Xu, Qidong (CN); Xiaoming Yang, Nanjing (CN); Meiling Ming, Nanjing (CN)

(73) Assignee: Nanjing Forestry University, Nanjing (CN)

( * ) Notice: Subject to any disclaimer, the term of this patent is extended or adjusted under 35 U.S.C. 154(b) by 0 days.

(21) Appl. No.: 18/825,366

(22) Filed: Sep. 5, 2024

(65) Prior Publication Data

US 2025/0092412 A1 Mar. 20, 2025

(30) Foreign Application Priority Data

Sep. 15, 2023 (CN) .......................... 202311195940.6

(51) Int. Cl.
*C12N 15/82* (2006.01)
(52) U.S. Cl.
CPC ..... *C12N 15/8262* (2013.01); *C12N 15/8205* (2013.01)
(58) Field of Classification Search
None
See application file for complete search history.

(56) References Cited

PUBLICATIONS

Qiu et al. DNA Research. 26(5). October. 423-431 (Year: 2019).*
GenBank Accession No. FM882126.1. Nardmann et al. (Year: 2009).*
CNIPA, Notification of First Office Action for CN202311195940.6, Mar. 27, 2024.
Nanjing Forestry University (Applicant), Replacement claims (allowed) of CN202311195940.6, Apr. 1, 2024.
CNIPA, Notification to grant patent right for invention in CN202311195940.6, Apr. 4, 2024.

* cited by examiner

*Primary Examiner* — Shubo Zhou
*Assistant Examiner* — David R Byrnes
(74) *Attorney, Agent, or Firm* — Hemisphere Law, PLLC; Zhigang Ma

(57) ABSTRACT

A *Ginkgo biloba* wuschel-related homeobox 3A (GbWOX3A) gene and an application thereof in plant tissue culture are provided. The GbWOX3A gene is derived from a *Ginkgo biloba* embryo, the gene sequence of the GbWOX3A gene is SEQ ID NO: 1, and the amino acid sequence encoded by the GbWOX3A gene is SEQ ID NO: 2. An expression of the GbWOX3A gene in developing embryo of *Ginkgo biloba* and regenerating a callus has specificity, and transgenic function verification experiments prove that overexpression of the GbWOX3A gene can promote regeneration of adventitious buds during the plant tissue culture. Therefore, the GbWOX3A gene has important theoretical significance and application value in the plant tissue culture, and especially plays an important role in improving the regeneration efficiency of gymnosperms.

1 Claim, 5 Drawing Sheets

Specification includes a Sequence Listing.

FIG. 2

GBWOX3A GENE AND APPLICATION THEREOF IN PLANT TISSUE CULTURE

CROSS-REFERENCE TO RELATED APPLICATION

This application claims priority to a Chinese patent application No. 202311195940.6, filed to China National Intellectual Property Administration (CNIPA) on Sep. 15, 2023, which is herein incorporated by reference in its entirety.

TECHNICAL FIELD

The disclosure relates to the field of plant genetic engineering technologies, particularly to a *Ginkgo biloba* wuschel-related homeobox 3A (GbWOX3A) gene and an application thereof in plant tissue culture.

STATEMENT REGARDING SEQUENCE LISTING

The sequence listing associated with this application is provided in text format in lieu of a paper copy and is hereby incorporated by reference into the specification. The name of the XML file containing the sequence listing is 24053THXT-USP1-SL.xml. The XML file is 12,074 bytes; is created on Sep. 2, 2024; and is being submitted electronically via patent center.

BACKGROUND

*Ginkgo biloba* is listed on the International Union for Conservation of Nature (IUCN) Red List of threatened species and is difficult to reproduce under natural conditions. Artificial propagation methods of the *Ginkgo biloba* mainly focus on cutting, tillering, grafting, artificial seeding, etc., and propagation periods of the artificial propagation methods are long, have a high cost, and are easily affected by the environment. Obtaining a large amount of regenerated seedlings from various ex vivo tissues of the *Ginkgo biloba* through tissue culture can overcome the defects of long propagation period, high cost, etc., reduce the workload, obtain a large amount of *Ginkgo biloba* seedlings in a short period of time, and improve seedling efficiency. Therefore, it is urgent to establish an efficient tissue culture regeneration system for *Ginkgo biloba* molecular breeding. However, so far, in the process of tissue culture regeneration, the induction rate of embryogenic callus is low and the embryogenic callus is prone to browning; non-embryogenic callus induces adventitious buds, indirectly making somatic embryogenesis difficult. A *Ginkgo biloba* genetic transformation system is also not successfully established, and therefore it is difficult to assist the regeneration of *Ginkgo biloba* through the transgenic technology and to improve the regeneration efficiency. Therefore, it is important to clarify the regulation and control mechanism of the process of the *Ginkgo biloba* tissue culture regeneration and promote the regeneration of the ex vivo tissue of the *Ginkgo biloba*.

Wuschel-related homeobox (WOX) gene family is a member of the homeobox superfamily in eukaryotic organisms and is a unique transcription factor in plants. The family members have a conservative homeodomain (HD) encoding 60-66 amino acids, and forming a helix-turn-helix (HTH) structure that can combine with deoxyribonucleic acid (DNA). The HTH structure plays an important role in maintaining the functional integrity of HD and is very conservative in different species. Researches show that the WOX gene has the functions of regulating plant embryo development and polarization, maintaining tissue stem cells, forming lateral organs and flower organs, stress response, etc., and particularly plays an important role in regulating cell proliferation and differentiation to promote plant tissue regeneration.

At present, the difficulty of in vitro regeneration limits the reproduction and genetic improvement of most woody plants (especially gymnosperms), and the function research of the WOX gene of the gymnosperms in the process of promoting plant tissue culture and regeneration has not been reported. Therefore, the key genes for improving the processes of tissue culture and regeneration in the gymnosperms are extremely important.

SUMMARY

Objectives of the present disclosure are to provide a *Ginkgo biloba* wuschel-related homeobox 3A (GbWOX3A) gene, which is derived from a *Ginkgo biloba* embryo, and an application of the GbWOX3A gene in plant tissue culture.

The present disclosure achieves the above objectives by the following technical solutions.

A first objective of the present disclosure is to provide the GbWOX3A gene, a gene sequence of which is SEQ ID NO: 1.

The GbWOX3A gene is derived from the *Ginkgo biloba* embryo.

An amino acid sequence encoded by the GbWOX3A gene is SEQ ID NO: 2.

A second objective of the present disclosure is to provide an application of the GbWOX3A gene in tissue culture of a plant.

In an embodiment, the application of the GbWOX3A gene in the tissue culture of the plant includes: overexpressing the GbWOX3A gene to promote a regeneration number of adventitious buds in the tissue culture of the plant.

In an embodiment, the plant is *Populus alba*× *Populus glandulosa* (Poplar 84K).

In an embodiment, a method for promoting the regeneration number of adventitious buds in the tissue culture of the poplar 84K includes the following steps: constructing an overexpression vector of pCAMBIA1302-GbWOX3A, transforming the overexpression vector pCAMBIA1302-GbWOX3A into an *Agrobacterium* EHA105 competent cell, and transforming a detached leaf of the poplar 84K by using *Agrobacterium*-mediated method.

The present disclosure has the following beneficial effects.

The present disclosure is cloned from the *Ginkgo biloba* embryo to obtain a coding sequence (CDS) of the GbWOX3A gene in the *Ginkgo biloba* WOX family; the expression of the GbWOX3A gene in the processes of *Ginkgo biloba* embryo development and embryogenic callus regeneration has specificity, and it is proved through the transgenic function verification experiments that the overexpression of GbWOX3A gene can promote regeneration of the adventitious buds in the plant tissue culture regeneration process. Therefore, the GbWOX3A gene is of important theoretical significance and has application value in the processes of tissue culture and regeneration for the plant; and especially plays an important role in improving the regeneration efficiency of gymnosperms.

BRIEF DESCRIPTION OF DRAWINGS

FIG. 2 illustrates a comparison diagram between a clone sequence of the GbWOX3A gene (SEQ ID NO: 3) and a genome prediction sequence of the GbWOX3A gene (SEQ ID NO: 1).

DETAILED DESCRIPTION OF EMBODIMENTS

Figure 1:
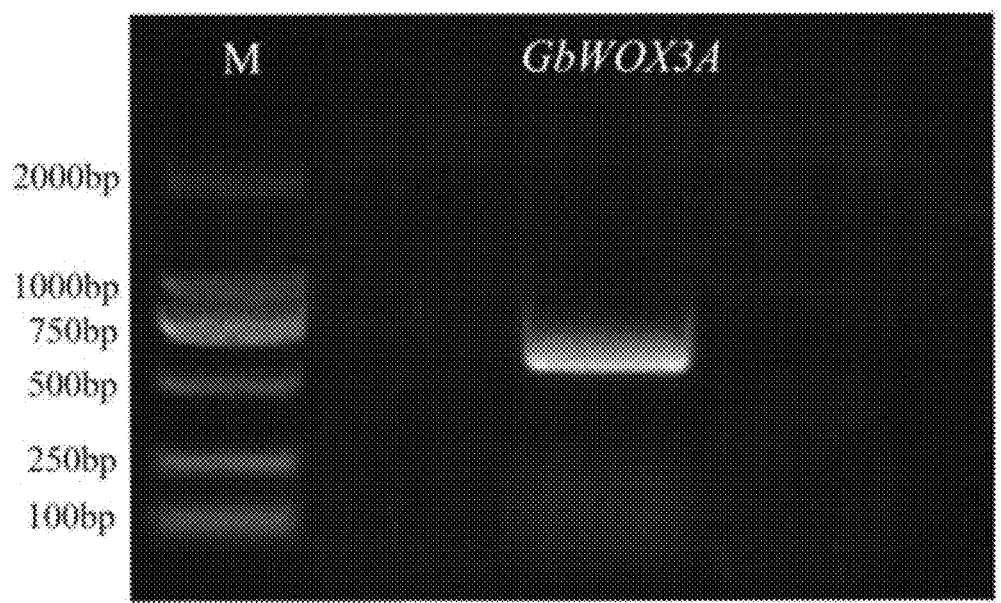
FIG. 1 illustrates a cloned full-length band of GbWOX3A gene, where M represents a DL2000 DNA Marker.

The present disclosure will be further described in detail below with reference to the attached drawings, and it is necessary to note that the following specific embodiments are only used to further describe the present disclosure and cannot be understood as a limitation to the protection scope of the present disclosure, and those skilled in the related art can make some non-essential improvements and adjustments to the present disclosure according to the above-described content.

1. Materials and Reagents

Experimental methods used in the present embodiment can be performed according to conventional methods unless specified. For example, conditions recited in Joseph Sambrook, etc., "*Molecular Cloning: A Laboratory Manual*" and Fredrick M. Ausubel, etc., "*Short Protocols in Molecular Biology*" are used in the present disclosure. In addition, the present disclosure is performed according to instructions provided by manufacturers of the used materials and reagents.

*Ginkgo biloba* embryos were collected from *Ginkgo biloba* gynoecious of about 40 years old planted in a garden experimental training center of Nanjing Forestry University on October 2021.

A ribonucleic acid (RNA) extraction kit and a plasmid extraction kit are purchased from Omega Bio-Tek Corporation, and their goods numbers are R6827 and D6943, respectively; a reverse transcription reagent is purchased from Monad Biotech Co., Ltd, and its goods number is MR05101M; a super-fidelity enzyme used for cloning polymerase chain reaction (PCR) is purchased from Takara Biomedical Technology (Beijing) Co. Ltd., and its goods number is D2215; a gel extraction kit is purchased from Vazyme Biological Technology Co. Ltd., and its goods number is DC301; 2× Rapid Taq Master Mix used in the common PCR is purchased from Vazyme Biological Technology Co. Ltd., and its goods number is P222; the restriction endonuclease NcoI and SpeI are purchased from TransGen Biotechnology Co. Ltd., and their goods numbers are JN101 and JS601 respectively; homologous recombinase is purchased from Vazyme Biological Technology Co. Ltd., and its goods number is C112; an expression vector of a specific plant is pCAMBIA1302-GFP; *Escherichia coli* DH5α and *Agrobacterium* EHA105 are all purchased from Tsingke Biotechnology Co., Ltd., and their goods numbers are TSC-C14 and TSC-A03, respectively; Murashige and Skoog (MS) and Luria-Bertani (LB, also referred to lysogeny broth) culture media are common culture media in the related art, and the formulations thereof refer to Joseph Sambrook, etc., "*Molecular Cloning: A Laboratory Manual*".

The materials, reagents, etc., used in the embodiments of the present disclosure can be obtained through commercial approaches, unless otherwise specified.

2. Methods 2.1 Full Length Cloning of GbWOX3A Gene

RNA of the *Ginkgo biloba* embryo is extracted by using an RNA extraction kit, and the extracted RNA of the *Ginkgo biloba* embryo is subjected to agarose gel electrophoresis to check the integrity of RNA; then, concentration and purity of RNA of the *Ginkgo biloba* embryo are detected by NanoDrop 2000 (referred to a micro volume spectrophotometer), and then the extracted RNA of the *Ginkgo biloba* embryo is placed at −80 degrees Celsius (° C.) for later use. Reverse transcription is performed on the extracted RNA of the *Ginkgo biloba* embryo by using the reverse transcription reagent purchased from Monad Biotech Co., Ltd to obtain complementary DNA (cDNA) of the *Ginkgo biloba* embryo. Information related to CDS of the GbWOX3A gene is searched in the whole genome CDS file of *Ginkgo biloba*, and OLIGO primer analysis software is used to design a forward primer of the full length cloning according to the sequence information to obtain a gene sequence 5'-ATGCCGATAACCAAAAATTAGCC-3' as SEQ ID NO: 4 and a reverse primer with a gene sequence 5'-TCATAGCCACTAACAGTGGAAAC-3' as SEQ ID NO: 5; and a forward primer with a homology arm is designed according to an on-line website (e.g., single-fragment cloning of tool of Vazyme) to obtain a gene sequence 5'-acgggggactcttgac-cATGCCGATAACCAAAAATTACTTAGGC-3' as SEQ ID NO: 6 and a reverse primer with a homology arm is designed to obtain a gene sequence 5'-aagttcttctccttttactagtTAAGC-CACTACACAGTGGAAAC-3' as SEQ ID NO: 7.

Figure 3:
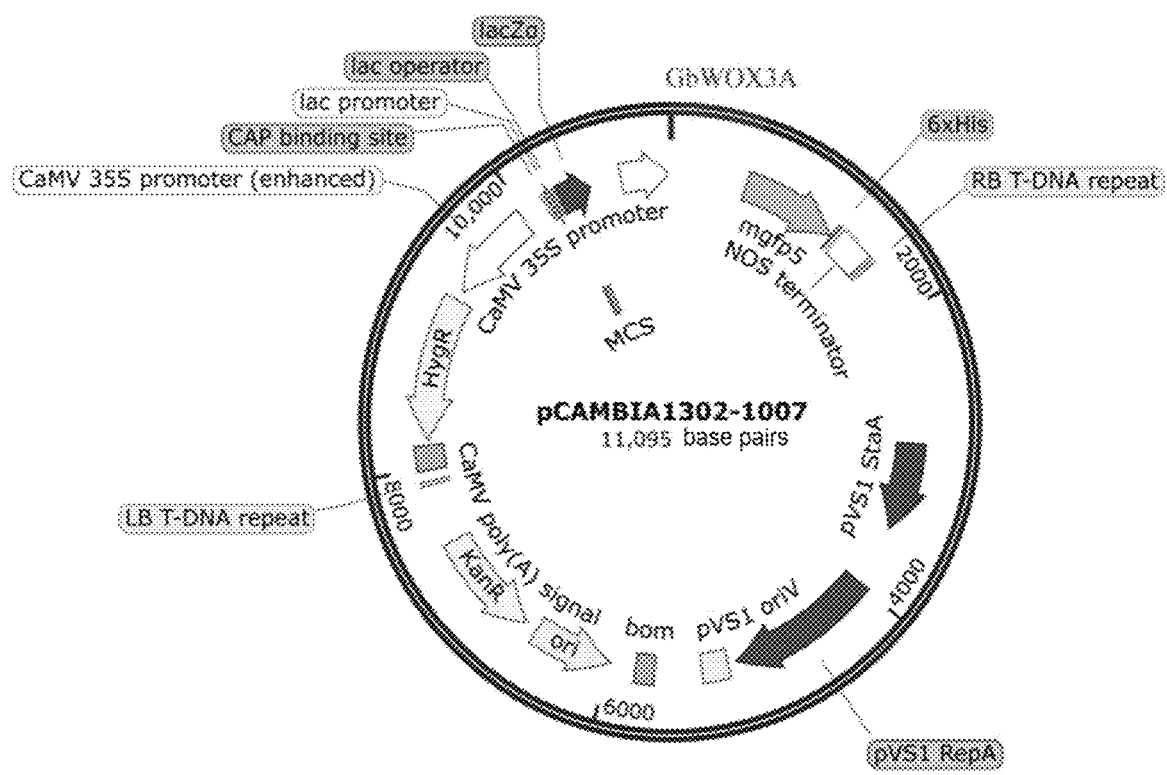
FIG. 3 illustrates a schematic diagram of an overexpressed vector pCAMBIA1302-GbWOX3A.

The cDNA is used as a template and then subjected to amplification by using the super-fidelity enzyme according to PCR. The PCR procedures are as follows: pre-denaturation at 98° C. for 3 minutes (min); then 35 cycles, including denaturation at 98° C. for 10 seconds(s), annealing at 58° C. for 5 s, and extension at 72° C. for 1 min; and finally extension at 72° C. for 5 min are performed to obtain a PCR product. After the PCR is completed, the PCR product is subjected to electrophoresis detection (with reference to FIG. 1), and the PCR product is recovered using the gel extraction kit to obtain recovered fragments. The recovered fragments are subjected to secondary PCR with the same procedures by using the primers with the homology arm and recovered to obtain a secondary PCR product. The expression vector pCAMBIA1302-GFP is subjected to double digests with restriction endonucleases, i.e., Nco I and Spe I, and procedures for the double digests with restriction endonuclease are as follows: performing incubation on the expression vector pCAMBIA1302-GFP at 37° C. for 15 min, followed by heating at 80° C. for 20 min to terminate the procedure for the double digests with restriction endonuclease to obtain a linearized pCAMBIA1302-GFP vector. The linearized pCAMBIA1302-GFP vector and the secondary PCR product are recombined at 37° C. under an action of homologous recombinase for 30 min to obtain a recombinant product. After the recombination, the recombinant product is transferred to an *Escherichia coli* DH5α competent cell to obtain a resuscitation fluid, the transformation steps thereof are shown in the description of the competent cell, and finally, the resuscitation fluid is uniformly coated onto the LB solid culture medium with kanamycin (Kana) resistance, and the LB culture medium is performed an inverted cultivation at 37° C. for 16 hours (h). Then, after the inverted cultivation is finished, a monoclonal colony in the LB culture medium is selected to identify, including: firstly using a sterile toothpick to obtain the monoclonal colony, mixing the monoclonal colony in 10 microliters (μL) of sterile water evenly to obtain a bacterial solution, then pipette 2 μL of the bacterial solution for PCR identification, and placing remaining 8 μL of the bacterial solution at 4° C. The PCR identification of the bacterial solution is performed by using the 2× Rapid Taq Master Mix, and PCR procedures thereof are as follows: pre-denaturation at 95° C. for 3 min, then 35 cycles, including: denaturation at 95° C. for 15 s, annealing at 58° C. for 15 s, and extension at 72° C. for 15 s, and finally extension at 72° C. for 5 min is carried out. Thereafter, the remaining 8 μL of the bacterial solution that is successfully identified by the PCR is delivered to Beijing Tsingke Biotech Co., Ltd and is used for sequencing and identifying whether the target segment is completely cloned successfully. Sequence comparison (with reference to FIG. 2) is performed by using DNAMAN software, and the successfully compared bacterial solution is expanded and cultured at 37° C. and 200 revolutions per minute (rpm), thereby performing plasmid extraction, and extraction steps of the plasmid refer to the description, and the obtained pCAMBIA1302-GbWOX3A plasmid (with reference to FIG. 3) is stored at −20° C. The target fragment is amplified to obtain the gene sequence of the GbWOX3A gene as shown in SEQ ID NO: 1, which is 561 base pairs (bp) in length, and then the gene sequence of the GbWOX3A gene is encoded to obtain 186 amino acids, and the amino acid sequence of the amino acids encoded by the GbWOX3A gene is illustrated as SEQ ID NO: 2.

2.2 Expression Mode of GbWOX3A Gene in Processes of Development and In Vitro Regeneration of the *Ginkgo biloba* Embryo A female *Ginkgo biloba* with an age of about 40 years was collected from September to November of 2021 at a landscape experimental training center of Nanjing Forestry University to obtain seeds. The seeds are divided into 5 grades according to a length of the *Ginkgo biloba* embryo. The *Ginkgo biloba* embryo selected at the fifth stage is inoculated into an Agar medium (referred to nutrient Agar) with Murashige and Skoog basal salt mixture (MS)+1 milligram per liter (mg/L), 6-benzylaminopurine (6-BA)+1 mg/L, naphthalene acetic acid (NAA)+30 grams per liter (g/L), and sucrose+7 g/L for callus induction, potential of hydrogen (pH) of the Agar medium is 5.8, a temperature thereof is 25° C., and the Agar medium is performed by light culture after 15 days of dark culture. The callus samples in five stages of the *Ginkgo biloba* embryo are collected, including: development of the cotyledon before the formation of callus (7 days after inoculation), an early stage of callus formation (15 days after inoculation), and callus proliferation stages (25 days, 36 days, and 54 days after inoculation respectively). Samples are taken from the five stages of the *Ginkgo biloba* embryo (i.e., embryos 1-5 abbreviated as Em1-Em5), two stages of endosperm (abbreviated as En1 and En5 respectively), and five stages of callus (abbreviated as $C_1$-$C_5$), each of which has three biological replicates, and then the samples are rapidly frozen in liquid nitrogen and stored in a −80° C. refrigerator. Thereafter, the samples are used for quantitative real-time PCR (qRT-PCR) analysis of transcriptome sequencing (RNA-seq) and GbWOX3A gene expression.

The steps for RNA extraction and reverse transcription are the same as 2.1, and the qRT-PCR is performed by using Applied Biosystems (ABI) 7500 real-time PCR Systems (also referred to a third generation of thermocycling technology) according to description of MonAmp™ SYBR® Green qPCR Mix with a goods number of MQ10201. Three biological replicates and three technical replicates are set up for the experiment. glyceraldehyde-3-phosphate dehydrogenase (GAPDH) gene of *Ginkgo biloba* is used as a reference gene, an upstream primer of the reference gene for the qRT-PCR is 5'-ATCCACGGGAGTCTTCAC-3' as SEQ ID NO: 8, and a downstream primer of the reference gene for the qRT-PCR is 5'-CTCATTCACGCCAACAAC-3' as SEQ ID NO: 9; and an upstream primer of the qRT-PCR of GbWOX3A gene designed by PrimerPremier 6 is 5'-CCAGAATCACAAAGCCAGGGATAGG-3' as SEQ ID NO: 10, and a downstream primer is 5'-TCCATTCCTTCTTCACCTCATCTGC-3' as SEQ ID NO: 11. A reaction system for the qRT-PCR is shown in the following Table 1.

TABLE 1

| qRT-PCR reaction system | |
| --- | --- |
| Reagent | Dosage |
| MonAmp ™SYBR ® Green qPCR Mix | 10 μL |
| Forward primer (10 μM) | 0.4 μL |
| Reverse primer (10 μM) | 0.4 μL |
| cDNA template | 1 μL |
| ddH$_2$O | 8.2 μL |

Figure 4:
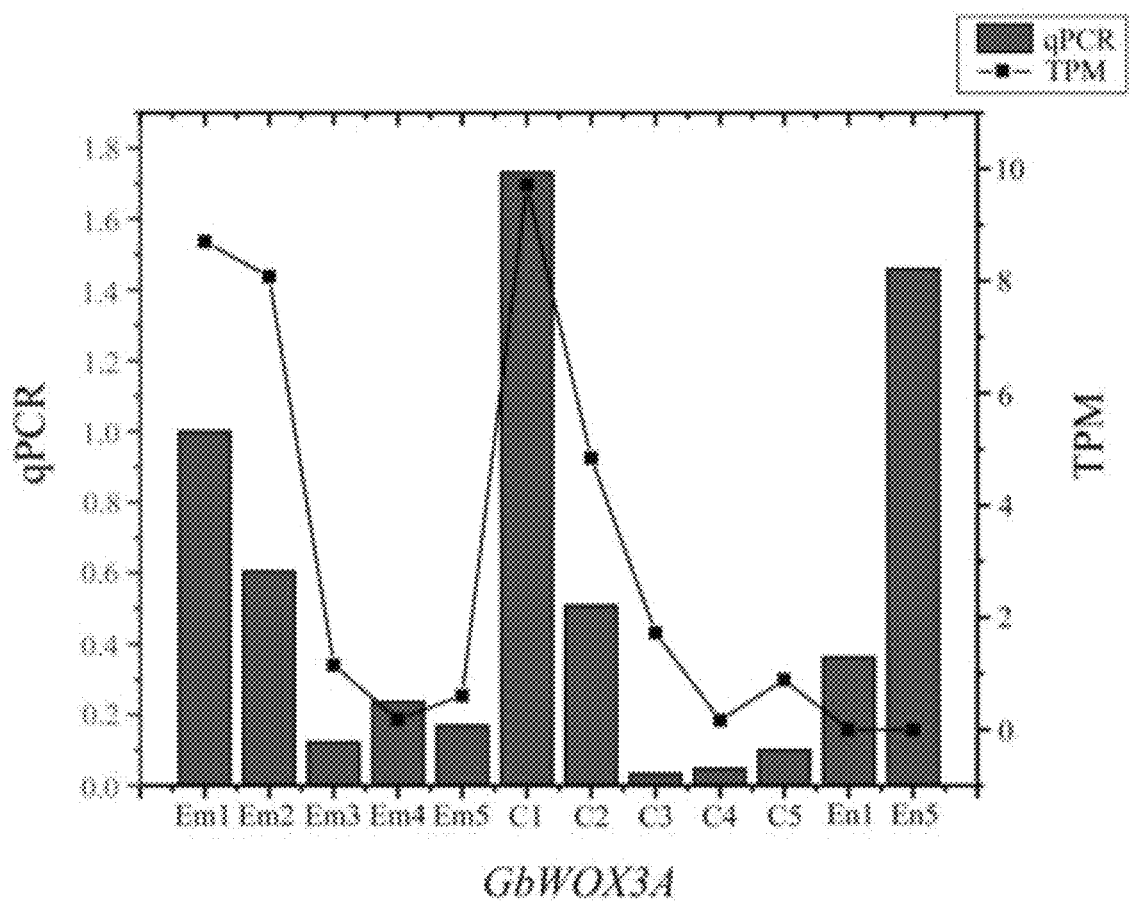
FIG. 4 illustrates a schematic diagram of expression patterns of the GbWOX3A gene in embryos and calli at different stages.

Procedures for the qRT-PCR are set to include: pre-denaturation at 95° C. for 30 s, denaturation at 95° C. for 10 s, annealing at 58° C. for 10 s, and extension at 72° C. for 30 s; and there are 40 cycles for the denaturation, the annealing, and the extension. Results of fluorescence quantification are calculated by 2-AACT method to determine the relative quantitative expression level of GbWOX3A gene. The results show that, as shown in FIG. 4, the GbWOX3A gene is primarily expressed in the early development stage and the callus formation of the *Ginkgo biloba* embryo.

3. Effect of Overexpressed GbWOX3A Gene on In Vitro Regeneration of Poplar 84K 3.1 Transformation of Recombinant Plasmid pCAMBIA1302-GbWOX3A into *Agrobacterium* EHA 105 Competent Cell With reference to the description of the EHA105 Chemically Competent Cell purchased from Tsingke Biotechnology Co., Ltd., the pCAMBIA1302-GbWOX3A is transformed into the *Agrobacterium* EHA 105 competent cell by using a freeze-thaw method as follows:

(1) The *Agrobacterium* EHA 105 competent cell stored at −80° C. is placed on ice to be melted into an ice-water mixture, and then the ice-water mixture is added with 1 μL of the recombinant plasmid, the recombinant plasmid is gently mixed with the ice-water mixture to obtain a mixture, and the mixture is left to stand on ice for 5 min, liquid nitrogen for 5 min, water bath at 37° C. for 5 min, and ice bath for 5 min in sequence.

(2) 700 μL of an antibiotic-free LB liquid medium is added to a centrifuge tube to obtain a mixture, and the mixture is resuscitated at 28° C. and 200 rpm for 3 h after uniform mixing to obtain a resuscitation fluid.

(3) The resuscitation fluid is applied evenly onto the LB solid culture medium containing Kana and rifampicin (Rif) resistance, the plate (also referred to the LB solid culture medium) is inverted and placed at 28° C. for 3 days, and then monoclonal identification is carried out, and the identification steps are the same as 2.1.

A colony that can be amplified to obtain the target band is a positive clone, the positive clone is cultured to OD600 (referred to optical density at 600 nanometers abbreviated as nm) of about 1 on a Kana-LB liquid medium with a concentration of 50 mg/L, 50% sterile glycerol is added into the Kana-LB liquid medium, the liquid nitrogen is quickly frozen for 2 min on the Kana-LB liquid medium, and stored for later use at −80° C.

3.2 Genetic Transformation of *Agrobacterium*-Mediated Poplar 84K Leaves

The top 5 leaves in a top end of an aseptic seedling of poplar 84K (also referred to *Populus alba× Populus glandulosa*) are taken to be cut into pieces (containing vein) with a size of 1 square centimeter ($cm^2$), and then the pieces are inoculated into an Agar medium containing a woody plant medium (WPM)+0.1 mg/L, kinetin (KT)+1.5 mg/L, 2, 4-D (referred to a herbicide that controls broadleaf weeds)+0.5 g/L, 4-morpholineethanesulfonic acid (MES)+20 g/L, and sucrose+7 g/L, and then are pre-cultured in the dark at 25° C. for 2 days. The *Agrobacterium*-mediated method is used for the transformation; the *Agrobacterium* bacterium solution is shaken to OD600 at 28° C. to about 0.6, and the *Agrobacterium* bacterium solution is resuspended with MS liquid according to an equal volume as the *Agrobacterium* bacterium solution. The pre-cultured leaves are placed in the resuspended solution for infection for 10-15 min, and excess bacterium solution on the surface of the pre-cultured leaves is dried and then the dried pre-cultured leaves are inoculated to WPM+0.1 mg/L, KT+1.5 mg/L, 2, 4-D+0.5 g/L, MES+20 g/L, sucrose 7 g/L, and Agar+100 μM AS to be cultured in dark light at 25° C. After 2 days, the leaves are transferred to WPM+0.1 mg/L, KT+1.5 mg/L, 2, 4-D+0.5 g/L, MES+20 g/L, sucrose+7 g/L, Agar+2 mg/L, hygromycin (hyg)+200 mg/L, cefotaxime sodium (CEF)+200 mg/L ticarcillin and clavulanate (Timentin®) to perform callus induction and screening. After 30 days, the leaves are transferred to MS+0.1 mg/L, NAA+1.0 mg/L, 6-BA+0.5 mg/L, MES+20 g/L, sucrose+7 g/L, Agar+1.5 mg/L, hyg+200 mg/L, CEF+200 mg/L, and Timentin® for differentiation culture. After 15 days of infection, a healing rate (calculated by callus block number/explant number) is counted, an induction rate of adventitious buds (calculated by adventitious bud number/explant number) is counted after 76 days, and the data is shown in the following Table 2.

Figure 5:
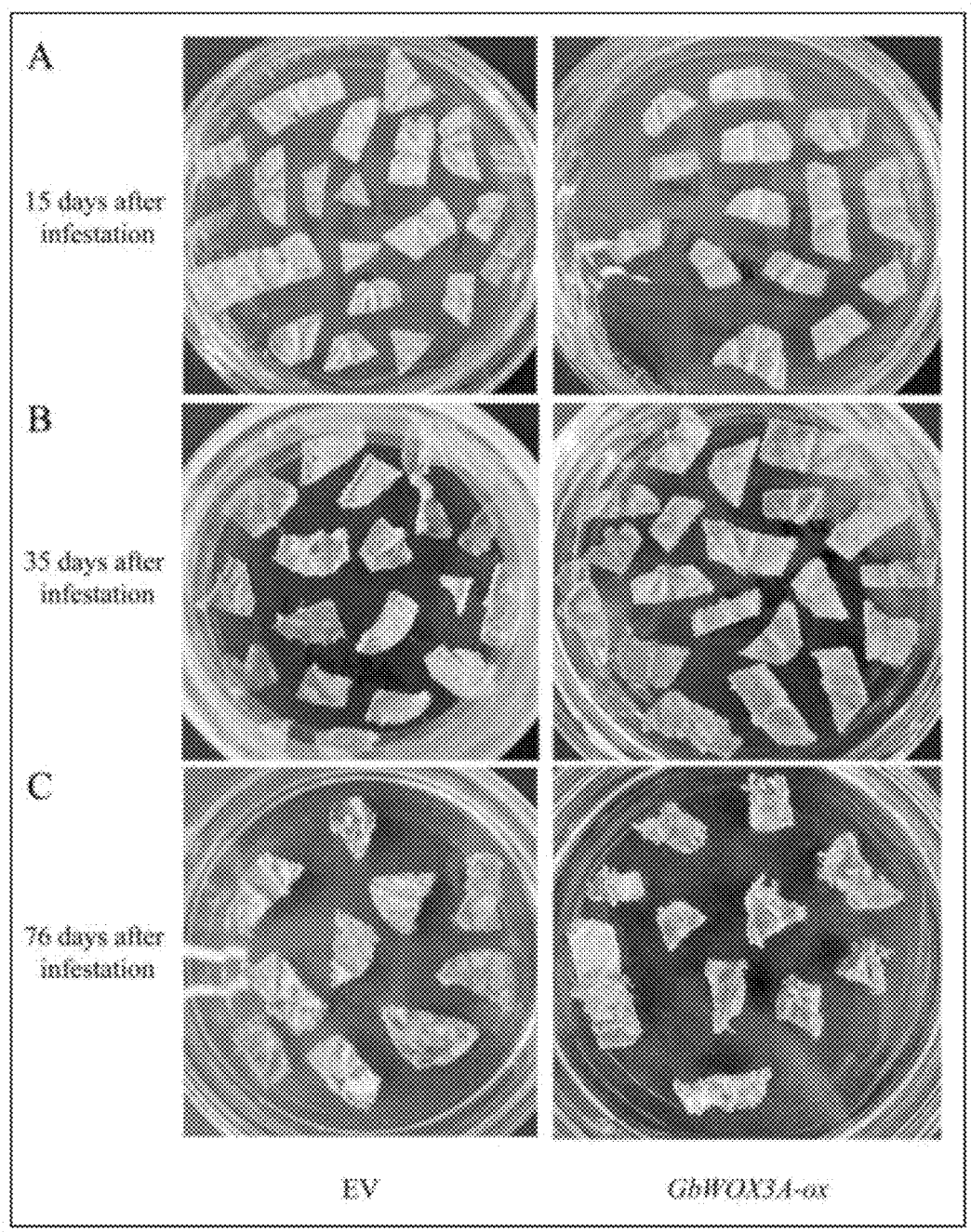
FIG. 5 illustrates a comparison diagram of transformation processes between overexpressed GbWOX3A gene and a mock control vector pCAMBIA1302-GFP in poplar 84K.

3.3 Effect of Overexpressed GbWOX3A Gene on Tissue Culture Regeneration Process of Poplar 84K As shown in FIG. 5, a mock control vector pCAMBIA1302-GFP (referred to EV) and the transgenic group pCAMBIA1302-GbWOX3A show consistent healing time and adventitious bud formation time, but there is a difference in the number of regenerated adventitious buds. The calli are induced on 15 days after infestation, and the calli are formed in most explants on about 35 days after infestation, and the adventitious buds of poplar 84K are regenerated on about 76 days after the *Agrobacterium* infestation. The EV and the GbWOX3A gene result in moderate texture and volume of calli, with a blue-green color and a 100% healing rate.

However, as shown in above Table 2, the GbWOX3A gene has a prominent effect in inducting the adventitious buds, which achieves up to 47.2%; and the induction rate of the adventitious buds in view of the EV is 24.7%. Meanwhile, it is worth noting that the GbWOX3A gene induces 5-6 times more adventitious buds per explant than the EV. This result demonstrates the important function of GbWOX3A gene in the in vitro regeneration induction of adventitious buds, thus providing the possibility for improving *Ginkgo biloba* tissue culture regeneration.

The above-mentioned embodiments only express several embodiments of the present disclosure, and the description thereof is relatively specific and detailed, but cannot be understood as a limitation to the scope of the protection of the present disclosure. It should be noted that, for those skilled in the related art, several modifications and improvements may be made without departing from the concept of the present disclosure, which all fall within the scope of the protection of the present disclosure.

TABLE 2

Data for callus formation and adventitious bud regeneration

| Gene | Classification | Data | | | | | | | | Summary |
|---|---|---|---|---|---|---|---|---|---|---|
| EV | Number of dishes | | | | 8 | | | | | |
| | Explant number | 10 | 10 | 12 | 8 | 9 | 12 | 8 | 12 | 81 |
| | Explant number with callus | 10 | 10 | 12 | 8 | 9 | 12 | 8 | 12 | 81 |
| | Frequency of callus induction | 100 | 100 | 100 | 100 | 100 | 100 | 100 | 100 | 100 |
| | Number of adventitious buds | 3 | 2 | 1 | 3 | 2 | 2 | 3 | 4 | 20 |
| | Induction rate of adventitious buds/% | 30 | 20 | 8.33 | 37.5 | 22.22 | 16.67 | 37.5 | 33.3 | 24.7 |
| GbWOX3A | Number of dishes | | | | 7 | | | | | |
| | Explant number | 11 | 8 | 11 | 9 | 9 | 13 | 11 | | 72 |
| | Explant number with callus | 11 | 8 | 11 | 9 | 9 | 13 | 11 | | 72 |
| | Frequency of callus induction | 100 | 100 | 100 | 10 | 100 | 100 | 100 | | 100 |
| | Number of adventitious buds | 5 | 4 | 5 | 7 | 4 | 5 | 4 | | 34 |
| | Induction rate of adventitious buds | 45.5 | 50 | 45.5 | 77.8 | 44.4 | 38.5 | 36.4 | | 47.2 |

What is claimed is:

1. An expression method of a GbWOX3A gene, comprising:

constructing an overexpression vector of pCAMBIA1302-GbWOX3A, transforming the overexpression vector pCAMBIA1302-GbWOX3A into an *Agrobacterium* EHA105 competent cell, and transforming a detached leaf of poplar 84K by using an *Agrobacterium*-mediated method to over-express the GbWOX3A gene in the detached leaf of the poplar 84K for a tissue culture regeneration of the poplar 84K; and wherein the gene sequence of the GbWOX3A gene is SEQ ID NO: 1, and the amino acid sequence encoded by the GbWOX3A gene is SEQ ID NO: 2.

* * * * *

SEQUENCE LISTING

```
Sequence total quantity: 11
SEQ ID NO: 1            moltype = DNA   length = 561
FEATURE                 Location/Qualifiers
source                  1..561
                        mol_type = other DNA
                        organism = synthetic construct
SEQUENCE: 1
atgccgataa ccaaaaatta cttaggcatt ccaaagacca tggagaatga tggggacaat    60
attggtgttg tttcaaaggc ccgtgctact cgagtttcag ctggcgctac gcctcagcct   120
tcgactacac gatggaaccc aacgtcagag cagctgatga tacttgaaga catgtacaga   180
ggtgggattc gaaccccaa tgctgatcag atacagcaaa tcacagcgca cttgagttta   240
tatgaaaaa ttgagggcaa gaatgtgttt tactggttcc agaatcacaa agccagggat   300
aggcagaaga tgcgtcgtaa aaatatggat aataacaaac aggagatgtc gggcaccttg   360
caagatcagg tatctcctgc agatgaggtg aagaaggaat ggaagttgga cataaattca   420
acagaagaat gctgtaaatc aataagctca tgtgggagta tggagcatga ttgggccgag   480
gttgatactg catctgatat gacctcaaga atcaggcctc taacaactct agaactgttt   540
ccactgtgta gtggcttatg a                                             561

SEQ ID NO: 2            moltype = AA   length = 186
FEATURE                 Location/Qualifiers
source                  1..186
                        mol_type = protein
                        organism = synthetic construct
SEQUENCE: 2
MPITKNYLGI PKTMENDGDN IGVVSKARAT RVSAGATPQP STTRWNPTSE QLMILEDMYR     60
GGIRTPNADQ IQQITAHLSL YGKIEGKNVF YWFQNHKARD RQKMRRKNMD NNKQEMSGTL    120
QDQVSPADEV KKEWKLDINS TEECCKSISS CGSMEHDWAE VDTASDMTSR IRPLTTLELF    180
PLCSGL                                                               186

SEQ ID NO: 3            moltype = DNA   length = 800
FEATURE                 Location/Qualifiers
source                  1..800
                        mol_type = other DNA
                        organism = synthetic construct
SEQUENCE: 3
cagtggtccc aaagatggac ccccacccac gaggagcatc gtggaaaaag aagacgttcc     60
aaccacgtct tcaaagcaag tggattgatg tgatatctcc actgacgtaa gggatgacgc    120
acaatcccac tatccttcgc aagacccttc ctctatataa gagagtcatt tccattgaga    180
gaacacgggg gactcttgac catgccgata accaaaaatt acttaggcat tccaaagacc    240
atggagaatg atggggacaa tattggtgtt gtttcaaagg cccgtgctac tcgagtttca    300
gctggcgcta cgcctcagcc ttcgactaca cgatggaacc caacgtcaga gcagctgatg    360
atacttgaag acatgtacag aggtgggatt cgaaccccca atgctgatca gatacagcaa    420
atcacagcgc acttgagttt atatggaaaa attgagggca agaatgtgtt ttactggttc    480
cagaatcaca aagccaggga taggcagaag atgcgtcgta aaaatatgga taataacaaa    540
caggagatgt cgggcacctt gcaagatcag gtatctcctg cagatgaggt gaagaaggaa    600
tggaagttgg acataaattc aacagaagaa tgctgtaaat caataagctc atgtgggagt    660
atggagcatg attgggccga ggttgatact gcatctgata tgacctcaag aatcaggcct    720
ctaacaactc tagaactgtt tccactgtgt agtggcttaa ctagtaaagg agaagaactt    780
ttcactggag ttgtcccaat                                                800

SEQ ID NO: 4            moltype = DNA   length = 23
FEATURE                 Location/Qualifiers
source                  1..23
                        mol_type = other DNA
                        organism = synthetic construct
SEQUENCE: 4
atgccgataa ccaaaaatta gcc                                             23

SEQ ID NO: 5            moltype = DNA   length = 23
FEATURE                 Location/Qualifiers
source                  1..23
                        mol_type = other DNA
                        organism = synthetic construct
SEQUENCE: 5
tcatagccac taacagtgga aac                                             23

SEQ ID NO: 6            moltype = DNA   length = 44
FEATURE                 Location/Qualifiers
source                  1..44
                        mol_type = other DNA
                        organism = synthetic construct
SEQUENCE: 6
acgggggact cttgaccatg ccgataacca aaaattactt aggc                      44

SEQ ID NO: 7            moltype = DNA   length = 43
FEATURE                 Location/Qualifiers
source                  1..43
                        mol_type = other DNA
```

```
                        organism = synthetic construct
SEQUENCE: 7
aagttcttct cctttactag ttaagccact acacagtgga aac                43

SEQ ID NO: 8            moltype = DNA  length = 18
FEATURE                 Location/Qualifiers
source                  1..18
                        mol_type = other DNA
                        organism = synthetic construct
SEQUENCE: 8
atccacggga gtcttcac                                            18

SEQ ID NO: 9            moltype = DNA  length = 18
FEATURE                 Location/Qualifiers
source                  1..18
                        mol_type = other DNA
                        organism = synthetic construct
SEQUENCE: 9
ctcattcacg ccaacaac                                            18

SEQ ID NO: 10           moltype = DNA  length = 25
FEATURE                 Location/Qualifiers
source                  1..25
                        mol_type = other DNA
                        organism = synthetic construct
SEQUENCE: 10
ccagaatcac aaagccaggg atagg                                    25

SEQ ID NO: 11           moltype = DNA  length = 25
FEATURE                 Location/Qualifiers
source                  1..25
                        mol_type = other DNA
                        organism = synthetic construct
SEQUENCE: 11
tccattcctt cttcacctca tctgc                                    25
```